United States Patent
Gold et al.

(10) Patent No.: US 12,181,464 B2
(45) Date of Patent: Dec. 31, 2024

(54) SYSTEM AND METHOD FOR IDENTIFYING THE PRESENCE OF INSECTS

(71) Applicants: Robert S. Gold, Newburgh, IN (US); Joseph Maria Kumar Irudayaraj, Champaign, IL (US)

(72) Inventors: Robert S. Gold, Newburgh, IN (US); Joseph Maria Kumar Irudayaraj, Champaign, IL (US)

( * ) Notice: Subject to any disclaimer, the term of this patent is extended or adjusted under 35 U.S.C. 154(b) by 1335 days.

(21) Appl. No.: 16/431,312

(22) Filed: Jun. 4, 2019

(65) Prior Publication Data

US 2019/0364872 A1 Dec. 5, 2019

Related U.S. Application Data

(60) Provisional application No. 62/680,249, filed on Jun. 4, 2018.

(51) Int. Cl.

| | |
|---|---|
| *G01N 33/542* | (2006.01) |
| *A01M 1/02* | (2006.01) |
| *A01M 1/04* | (2006.01) |
| *A01M 1/10* | (2006.01) |
| *C12N 15/115* | (2010.01) |
| *G01N 33/53* | (2006.01) |

(52) U.S. Cl.
CPC ........... *G01N 33/542* (2013.01); *A01M 1/026* (2013.01); *A01M 1/103* (2013.01); *A01M 1/023* (2013.01); *A01M 1/04* (2013.01); *C12N 15/115* (2013.01); *C12N 2310/16* (2013.01); *G01N 33/5308* (2013.01); *G01N 2333/43552* (2013.01)

(58) Field of Classification Search
CPC ............. G01N 33/542; G01N 33/5308; G01N 2333/43552; A01M 1/026; A01M 1/103; A01M 1/023; A01M 1/04; C12N 15/115; C12N 2310/16; Y02A 50/30
See application file for complete search history.

(56) References Cited

U.S. PATENT DOCUMENTS

2013/0011836 A1* 1/2013 Colaizzi ............... C12Q 1/6888
435/287.2

OTHER PUBLICATIONS

Chen et al. (Food Chemistry 215 (2017) 377-382).*
Lerga et al.( Anal. Chem. 2019, 91, 7104-7111, including Supplemental p. S1-S7, published May 1, 2019).*
Gu et al. ("Biosensors Based on Aptamers and Enzymes", 2014, Springer, 331 pages).*
Quanyuan Wan, Xiaohui Liu, & Youli Zu, Oligonucleotide Aptamers for Pathogen Detection and Infectious Disease Control. Theranostics. 9133 (2021). Discusses the use of flurophores with oligonucleotides.

* cited by examiner

*Primary Examiner* — Nancy J Leith
*Assistant Examiner* — Jessica D Parisi
(74) *Attorney, Agent, or Firm* — Indiana University Maurer School of Law Intellectual Property Legal Clinic

(57) ABSTRACT

A system and method to detect the presence of bed bugs are disclosed. A system detecting the presence of bed bugs comprises an aptamer solution that includes a base ligand, a fluorophore ligand that includes at least one fluorophore, and a quencher ligand that includes at least one quencher, a liquid application tool, and a fluorescent light source. A method of detecting the presence of bed bugs, comprising providing a liquid application tool that carries an aptamer solution, applying the aptamer solution to a target area, shining fluorescent light on the target area, and observing the target area under the fluorescent light. If there are light spots under the fluorescent light, bed bugs have been present.

8 Claims, 4 Drawing Sheets

SYSTEM AND METHOD FOR IDENTIFYING THE PRESENCE OF INSECTS

RELATED APPLICATION

This application claims the benefit of U.S. Provisional Application No. 62/680,249 titled "A spray to identify bed bug infestations" to Robert Gold, filed Jun. 4, 2018, the entire disclosure of which is expressly incorporated by reference herein.

TECHNICAL FIELD

The present disclosure generally relates to the detection of substances. More particularly, the present disclosure relates to a system and method for identify the presence of substances indicative of unhealthy conditions.

BACKGROUND AND SUMMARY OF THE DISCLOSURE

On occasion, it is helpful to determine if particular substances are present that are indicative of unhealthy conditions. For example, it may be helpful to determine if an insect or other organism has been present at a location. Or, it may be helpful to determine if certain foods may no longer be safe to consume. The presence of such organism or potentially unsafe food may be determined by detecting compounds associated with the organisms or potentially unsafe food.

According to the present disclosure, a system for identity the presence of certain organisms or unsafe food is provided using a light source and compound delivered using a spray bottle, wipe, or other delivery system. The compound contains an aptamer having an affinity for a specific target compound, such as a substance associated with specific organisms or unsafe conditions, such as spoiled food. The aptamer is annealed or otherwise joined to a nucleotide strand. The strand is synthesized to include a light re-emitting substance, such as a fluorescent label, that re-emits light when excited, typically by a source of light. The aptamer is synthesized to include a light re-emitting suppressor that suppresses the re-emittance of the light when in close enough proximity to the light re-emitting substance. When the aptamer is joined to the strand, the suppressor suppresses the re-emittance of light by the light re-emitting substance. Thus, when a light is presence, the light re-emitting substance does not re-emitting the light. If the aptamer is exposed to its specific target compound, the aptamer is attracted to the specific target compound and dislodges the strand, moving the suppressor away from the light re-emitting substance. Thereafter, if light is present, the light re-emitting substance will re-emit the light, indicating the presence of the specific target compound.

According to the present disclosure, a method detecting the presence of certain organisms and unsafe conditions are also provided. The method includes providing a light source and aptamer having an affinity for a target compound are provided. The aptamer is delivered to an area to be analyzed. The light is emitted on the area. Re-emittance of the light indicates the presence of the target compound, which is associated with a certain organism or unsafe condition, which indicates that the organism or unsafe condition is presence or has been present in the area. The lack of such re-emittance of the light indicates the lack of such a target compound, which indicates the lack of the presence of the organism or unsafe condition then or in the recent past.

BRIEF DESCRIPTION OF THE DRAWINGS

The previously described aspects of this disclosure will grow to be appreciated at a greater level once references to the following accompanying illustrations are expounded upon.

Figure 1:
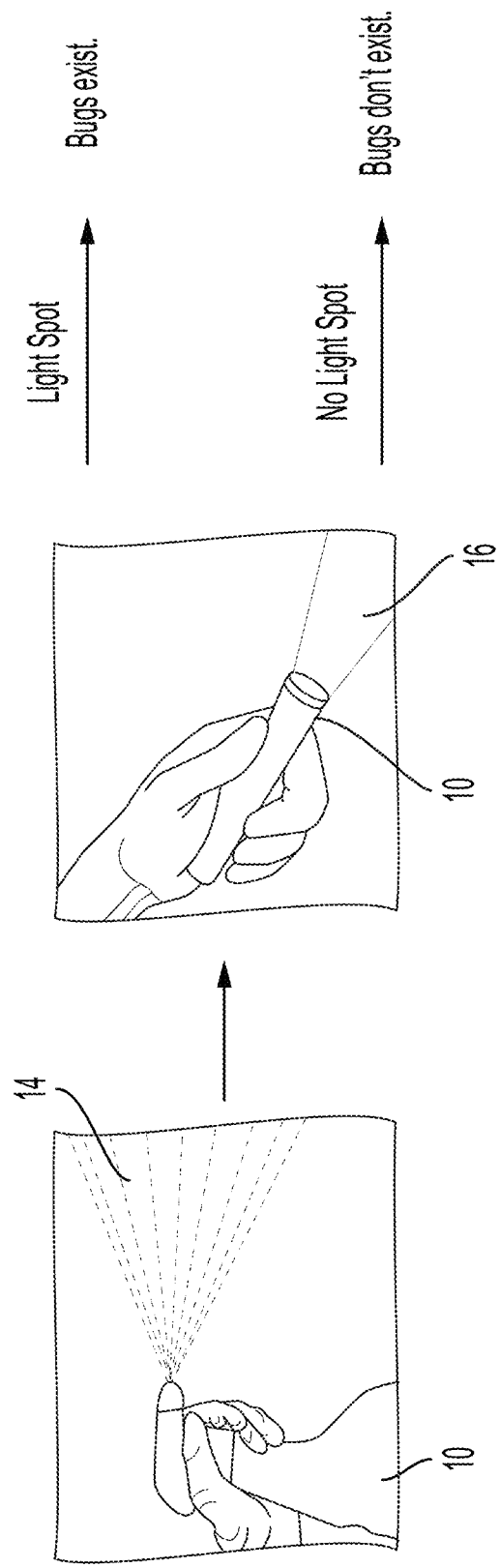
FIG. 1 is an overall view of a process of applying a spray to detect the presence of bed bugs.

The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the disclosure is thereby intended. The disclosure includes any alterations and further modifications in the illustrative devices and described methods and further applications of the principles of the disclosure which would normally occur to one skilled in the art to which the disclosure relates.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
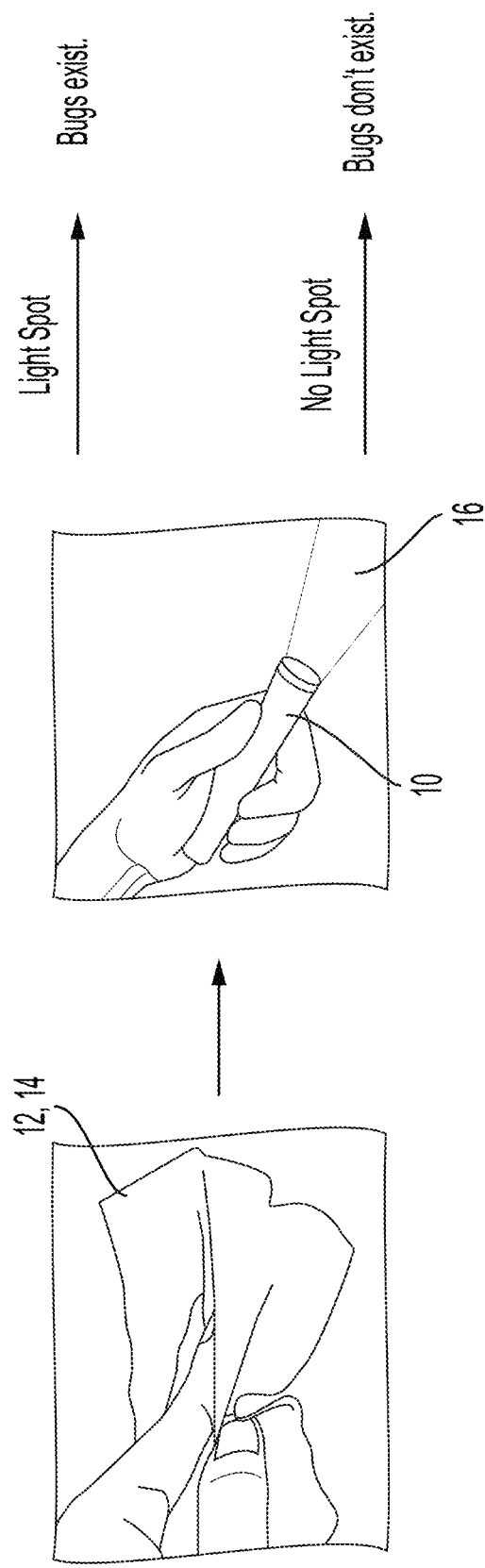
FIG. 2 is an overall view of a process of applying a wipe to detect bed bugs.

FIGS. 1 and 2 illustrate an overall view of a process of applying a compound 10 as a spray 12 with a spray bottle 14, a wipe 16, sponge (not shown), or other delivery system to a detection area and the application of light 16 by a light source, such as a flashlight 18 to detect insects (not shown in the figures).

Insects, such as bed bugs, lice, and fleas, are used to illustrate use of the systems and methods described herein to detect the presence of such insects. However, the systems and methods described herein can be used to detect the presence of other animals and organisms, such as bacteria including cdiff, staph, etc., and other substances, such as unsafe food including spoiled fish.

According to the present disclosure, compound 10 is a solution that includes a delivery medium, such as water or a buffer solution such as phosphate buffer saline and a substance 20 that has an active state that re-emits light in the presence of a target substance and passive state that suppresses re-emittance of light when the target substance is not present. The target substance is associated with a specific insect, such as a bed bug (or other organism or other item). When a bed bug enters an area, it deposits the target substance, such as bedbug excrement. If a user suspects a bed bug may be present or have been present in the area, the user applies solution 10 to the area to be tested using bottle 14, wipe 16, or other delivery system. If the bedbug excrement is present in the tested area, at least a portion of solution 10 changes from the passive state to the active state. If a light, such as flashlight 18, have a specific wavelength is shone on the tested area, the portion of solution 10 that is active will re-emit light, either at the same or a different wavelength. A user detecting the re-emitted light will know that bedbug excrement is present in the tested area, indicating that one or more bed bugs is present or has been present in the tested area. The failure to detect re-emitted light indicates that no bedbug excrement is present in the tested area, indicating that no bed bugs have been present in the tested area or the area, such as a bed sheet, has been sufficiently cleaned to remove bedbug excrement. According to one embodiment, a concentration range in the micro molar to pico molar is provided According to one aspect of the present disclosure, substance 20 includes a nucleotide strand in the form of an aptamer 22 that has an affinity for a target substance 24 associated with a specific insect, such as a bed bug. Example aptamers 22 include stable ssDNA or RNA ligands that can bind with high affinity and specificity to target substance 24, such as an antigen, or other small molecules, peptides, proteins (including nitrophorin, lice and other proteins discussed in U.S. patent application Ser. No. 16/176,483, titled "Test Strip to Identify Insect & Arachnid Ectoparasites, and other proteins), cells, and/or tissue associated with organisms including insects.

One such target substance is a component of bedbug excrement, such as histamine. An example aptamer 22 is a histamine aptamer, such as the H2 aptamer that has a high affinity for histamine. As mentioned above, this systems and methods described herein can be used to detect unsafe conditions including unsafe food. For example, a histamine aptamer can also be used to detect certain spoiled fish.

Solution 10 also includes a light re-emitting base in the form of a nucleotide strand 26. Strand 26 is synthesized to include a light re-emitting substance, such as a fluorophore ligand including a fluorophore 28, which re-emits light when exposed to a light source, such as flashlight 18, of a specific wavelength. The type of light 16 should be chosen depending on fluorophore 28 and may emit UV, blacklight, bluelight, any fluorescent, LED or any other lights. The re-emitted light may be at the same or different frequency as source light 16.

Figure 3:
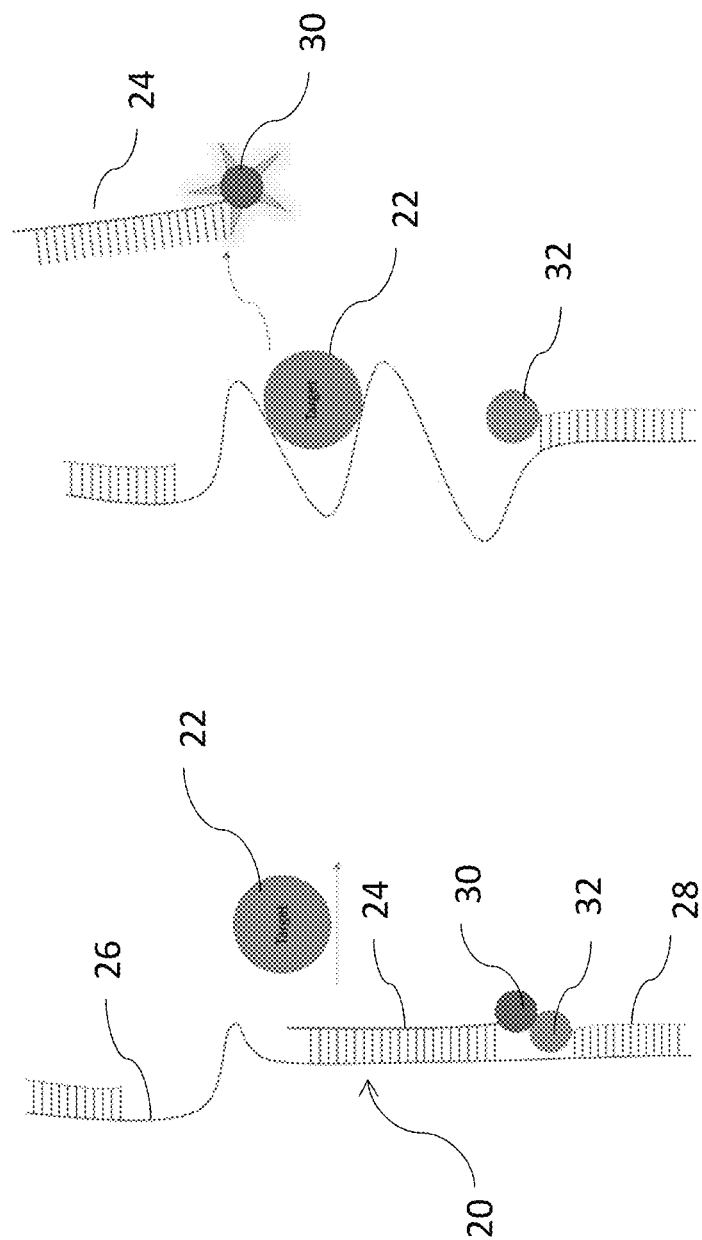
FIG. 3 is a view showing an aptamer being disjoined to a strand allowing for re-emittance of light.
Figure 4:
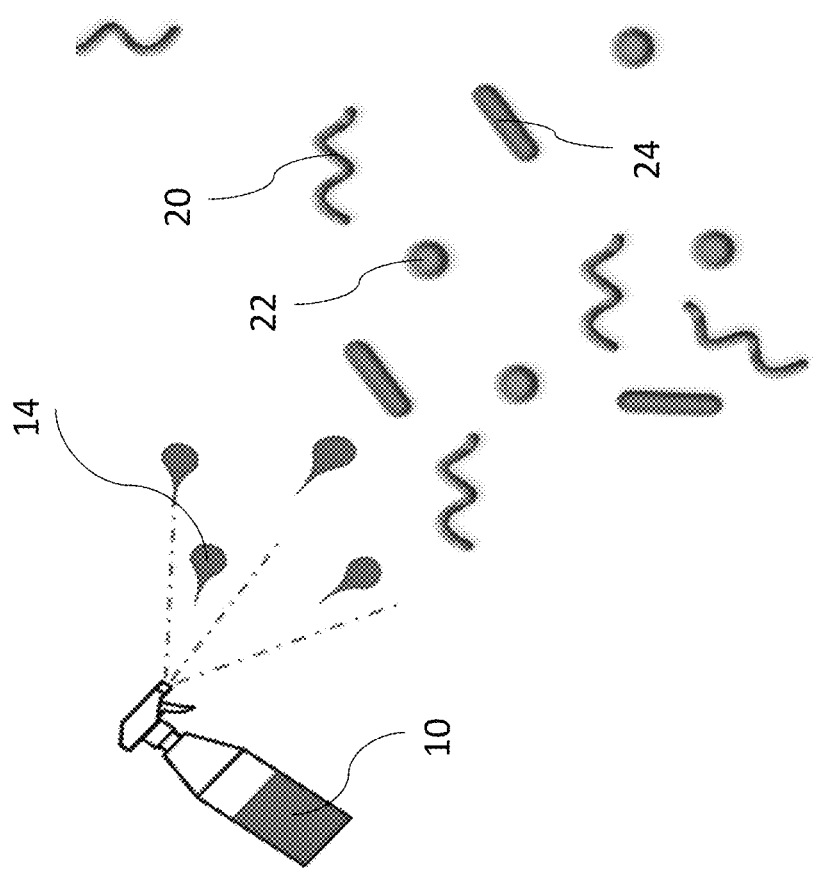
FIG. 4 is a view of compounds existing in a target area.

Aptamer 22 is synthesized to include a light re-emitting suppressor such as a quencher ligand including a quencher 30. According to one embodiment, fluorophores with an emission in the range between 500 and 550 nm such as FAM and HEX are quenched with quenchers with absorption maxima between 450 and 550 nm such as dabcyl and BHQ-1. According to another embodiment, fluorophores with emission above 550 nm such as rhodamines and Cy3/Cy5 are quenched with quenchers with absorption maxima above 550 nm such as Black Hole Quencher-2 or DDQ-II quencher. In the passive state of solution 10 mentioned above, nucleotide stand 26 is annealed or otherwise joined to aptamer 22 so that quencher 30 is in close enough proximity to fluorophore 28 to suppress or block its ability to re-emit light as shown in the left side of FIG. 3. According to one embodiment, nucleotide strand 26 includes quencher 30 and aptamer 22 includes fluorophore 28.

If light 16 from flashlight 18 shines on solution 10, fluorophore 28 in the portion of solution 10 in the passive state will not re-emitted light. A user that detects a lack of re-emitted light then knows that target substance 24 associated with the specific insect, such as a bed bug, is not present in the tested area. Based on this knowledge, the user knows the specific insect was likely not in the target area in the past or the target area has been sufficient cleaned to remove target substance 24.

As mentioned above, aptamer 22 has a high affinity for target substance 24. The affinity is so high, that nucleotide strand 26 will be dislodged from aptamer 22 when target 24 is in close enough proximity to aptamer 22 as shown in the right side of FIG. 3. Solution 10 with strand 26 dislodged is in the active state mentioned above so that quencher 30 is no longer close enough to fluorophore 28 to suppress or block its ability to re-emit light. Thus, if light 16 from flashlight 18 shines on solution 10, fluorophore 28 in the portion of solution 10 in the active state will re-emit light, such as blue, red, pink or some other color that was not re-emitted with quencher 30 was in close proximity to fluorospore 28. A user that detects the re-emitted light then knows that target substance 24 associated with the specific insect, such as a bed bug, is present in the tested area. Based on this knowledge, the user knows the specific insect was likely in the target area in the recent past. Based on this understanding, the user can arrange for treatment of the target area and surrounding area to eliminate the specific insect. After an attempt to eliminate the specific insect, the target area, such as a bed sheet, may be sufficiently cleaned to remove or degrade any remnant target substance 24. The target area may be subsequently tested for the presence of target substance 24 to detect insufficient cleaning of the target area, a new infestation, and/or unsuccessful elimination of the specific species.

According to the present disclosure a system and method is provided for detecting target 24 in a large volume liquid sample. Aptamer 22 are labeled with a fluorophore or horseradish proxidase (HRP) 28 for colorimetric sensing and functionalized (attached) to a nitrocellulose strip to capture target 24 in solution. Target 24 can be the excrement of a bedbug suspension. The capture of target 24 with aptamer 22 would release the HRP (or fluorophore) 28 labeled complementary DNA sequences into the solution. The ensuring fluorescence can be directly viewed by a fluorescence lamp 18. If a HRP 28 is provided, then reaction may be catalyzed by tetra methyl blue (TMB) to indicate the presence of target bacteria in liquid sample to produce a colorimetric signal, which could be recognized by naked eyes, or a more precise quantitative determination. As a combination of target enrichment and enzyme-based amplification of colorimetric signal, the proposed method facilitates the monitor of target in large volume liquid samples.

According to the present disclosure, a fluorescent aptamer-based biosensor is provided to be sprayed on solid samples. Graphene oxides are provided to quench the fluorescence from corresponding tags (Dong et al., 2010). With aptamer and graphene oxides, a biosensor for the detection of histamine target on solid samples, with a spray-based strategy is provided. The graphene oxides are modified with suitable polymers which increase their affinity to the surface. Aptamers hybridized with complementary sequences which are linked with fluorophore are conjugated to the graphene oxides. The fluorescence from the fluorophore is quenched by the graphene oxides due to fluorescence resonance energy transfer. The obtained modified graphene oxides with aptamer sequences as probes are then dispersed in suitable solutions. During detection, the probe solution is sprayed on the surface. The recognition of aptamer to target will release the fluorophore-labeled complementary sequence, which are collected by a suitable rinse step while the graphene oxides stay on the sample due to the affinity from polymer modification. The fluorescence from the fluorophore conjugated on complementary sequences would restore as the detectable signal for the presence of targets. The methods may be used on the solid sample, requiring no long and complex sampling process, thus fit for on-site detection of bed bugs.

According to present disclosure, a wet wipe-based aptamer sensor for the detection of a target on solid samples is provided. A wet wipe, which could provide a liquid environment for the aptamer-based recognition, is used as a biosensing platform for the detection of target 24 on the surface of solid samples. An aptamer-based fluorescent detection strategy is provided for the detection of target on solid samples. The recognition is based the corresponding aptamer, where fluorophore is conjugated to one end of aptamer sequence. A complementary sequence linked with nanoparticle or a quencher which quenches the fluorescence is hybridized with the aptamer, like the pattern proposed in the reported method (Lerga et al., 2019). Then, through aptamer sequence, the hybridized DNA sequences are linked to wet wipe, which contains a suitable solution for the stability and recognition activity of aptamer. The obtained wet wipe could be stored in sealed containers. During detection, the modified wet wipe covers on the solid samples and contact the surface compactly. With incubation, the capture of target with aptamer would detach the complementary sequence thus separate the nanoparticles and fluorophore on aptamer sequence. After incubation, the solid sample is removed and the wet wipe is illuminated with UV light. The fluorescence from the fluorophore would be restored for the determination of the existence of target bacteria on the surface of solid sample. Furthermore, by integrating culture media on the wet wipe, a pre-culture step could be used along with the proposed biosensor for improved sensitivity. Additional details are provided in Mairal Lerga, T.; Jauset-Rubio, M.; Skouridou, V.; Bashammakh, A. S. O.; El-Shahawi, M. S.; Al-Youbi, A. O.; O'Sullivan, C. K. Anal. Chem. 2019 and 2. Dong, H. F.; Gao, W. C.; Yan, F.; Ji, H. X.; Ju, H. X. Anal. Chem. 2010, 82, 5511-5517.

Those having ordinary skill in the art will recognize that numerous modifications can be made to the specific implementations described above. The implementations should not be limited to the particular limitations described. Other implementations may be possible.

We claim:

1. A compound including
an aptamer having an affinity for a-histamine associated with bed bug excrement,
a nucleotide strand, at least one quencher joined to at least one of the aptamer and the nucleotide strand, and
at least one fluorescent label wherein the fluorescent label is a fluorophore joined to at least one of the nucleotide strands and the aptamer, the compound being adapted to include a first state wherein the nucleotide strand is joined to the aptamer with the at least one quencher being in sufficiently close proximity to the fluorophore to suppress re-emittance of light by the fluorophore and a second state wherein the nucleotide strand is sufficiently dislodged from the aptamer with the quencher being sufficiency distance from the fluorophore to permit re-emittance of light by the fluorophore.

2. The compound of claim 1, wherein the aptamer is a histamine aptamer.

3. The compound of claim 1, wherein the fluorophore has an emission in the range between 500 and 550 nm.

4. The system of claim 3, wherein the container is a spray bottle.

5. The system of claim 3, wherein the container is a wipe.

6. The system of claim 3, wherein the light source is a fluorescent light source.

7. A solution comprising a liquid and the compound of claim 1.

8. A system for detecting bed bugs comprising a container, the solution of claim 7 positioned in the container, and a light source emitting a wavelength, wherein the at least one fluorescent label is configured to re-emit light in response to the wavelength when the compound is in the second state.

* * * * *